United States Patent [19]

Thompson, Sr.

[11] 4,312,339
[45] Jan. 26, 1982

[54] DEVICE FOR ADMINISTERING AN ANESTHETIC GAS

[75] Inventor: James W. Thompson, Sr., Horsham, Pa.

[73] Assignee: Porter Instrument Co., Inc., Hatfield, Pa.

[21] Appl. No.: 135,262

[22] Filed: Mar. 31, 1980

[51] Int. Cl.³ .......................................... A61M 16/00
[52] U.S. Cl. ............................. 128/205.25; 128/910; 137/DIG. 9
[58] Field of Search .............. 128/910, 201.27, 203.28, 128/203.29, 204.18, 205.12, 205.13, 205.17, 205.24, 205.25, 207.13, 205.19, 139, 276, 201.28; 137/510, 207, DIG. 8

[56] References Cited

U.S. PATENT DOCUMENTS

| | | | |
|---|---|---|---|
| 3,467,094 | 9/1969 | Goodman | 128/205.17 X |
| 3,537,447 | 11/1970 | Gauthier et al. | 128/910 X |
| 3,662,774 | 5/1972 | Johannisson et al. | 128/910 X |
| 3,721,239 | 3/1973 | Myers | 128/910 X |
| 4,015,598 | 4/1977 | Brown | 128/205.25 |
| 4,067,328 | 1/1978 | Manley | 128/910 |
| 4,137,912 | 2/1979 | O'Neill | 128/201.27 X |
| 4,219,020 | 8/1980 | Czajka | 128/207.13 |

FOREIGN PATENT DOCUMENTS 2213764 9/1973 Fed. Rep. of Germany ...... 128/910
2728723 12/1978 Fed. Rep. of Germany ...... 128/910

OTHER PUBLICATIONS

Air Products, Foreggor Catalog No. 7-351-005, "Seaveng-Or Gas Evacuator Illustrations", Jun. 1975.

*Primary Examiner*—Henry J. Recla
*Attorney, Agent, or Firm*—George J. Harding, 3rd

[57] ABSTRACT

A system for administering an anesthetic gas to a patient has a mask, means for supplying an anesthetic gas to the mask when the patient inhales, and an exhaust line having its proximal end connected to the mask and adapted to have its terminal end connected to a source of vacuum to exhaust gas from the mask when the patient exhales. A closed reservoir is in series with said exhaust line between the proximal and terminal ends thereof. The reservoir has an inlet and an outlet with a check valve adjacent to the inlet to prevent the flow of gas out of the reservoir through the inlet when the patient inhales. Advantageously, the reservoir check valve is a diaphragm valve and the face mask has at least one nozzle for scavenging gas escaping from the mask.

7 Claims, 12 Drawing Figures

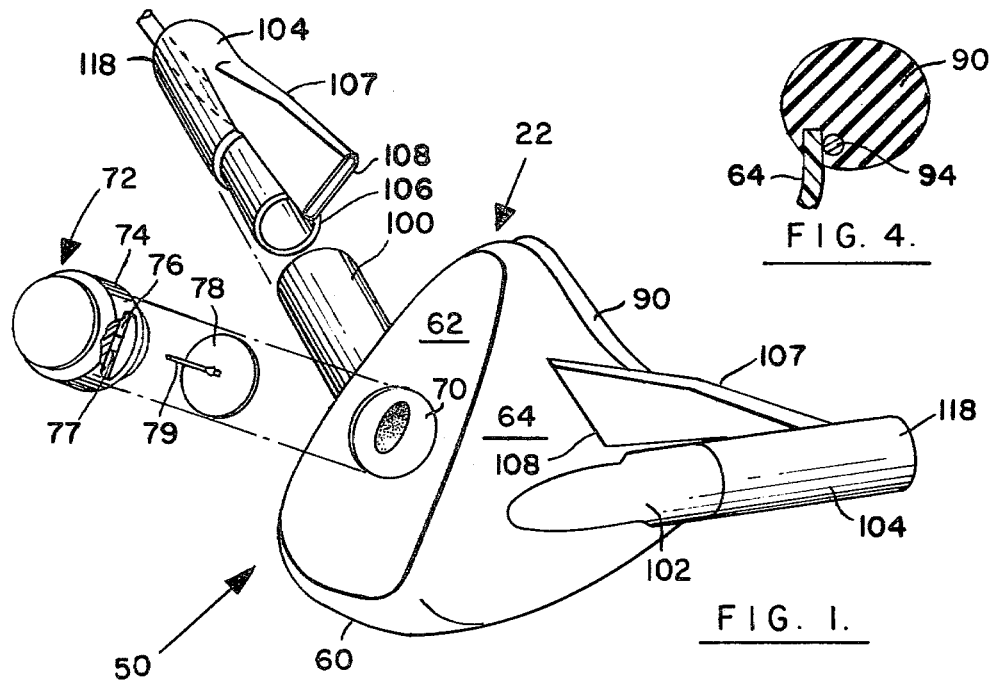
FIG. 1.
FIG. 4.
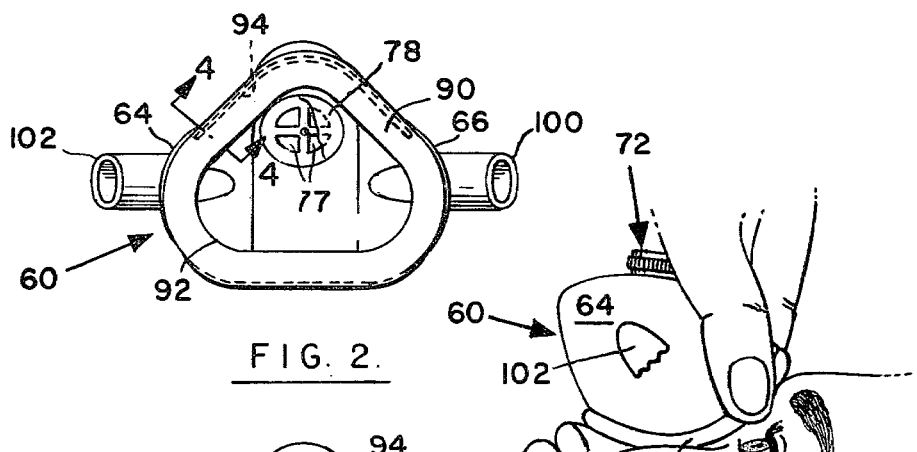
FIG. 2.
FIG. 5.
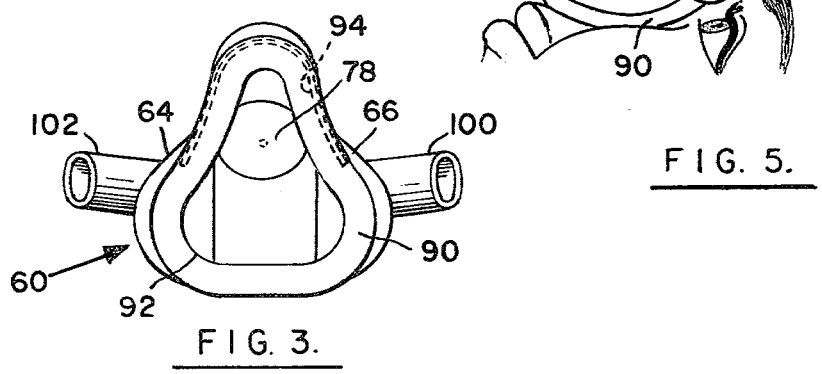
FIG. 3.

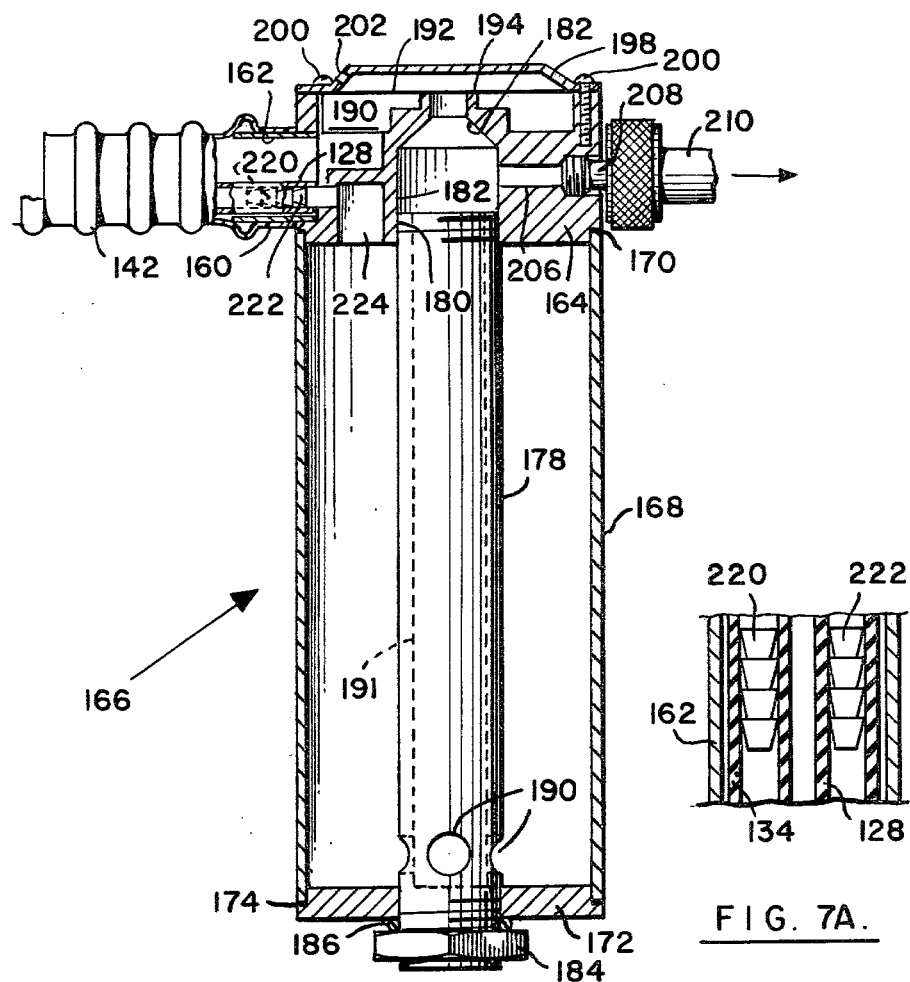
FIG. 7.
FIG. 7A.
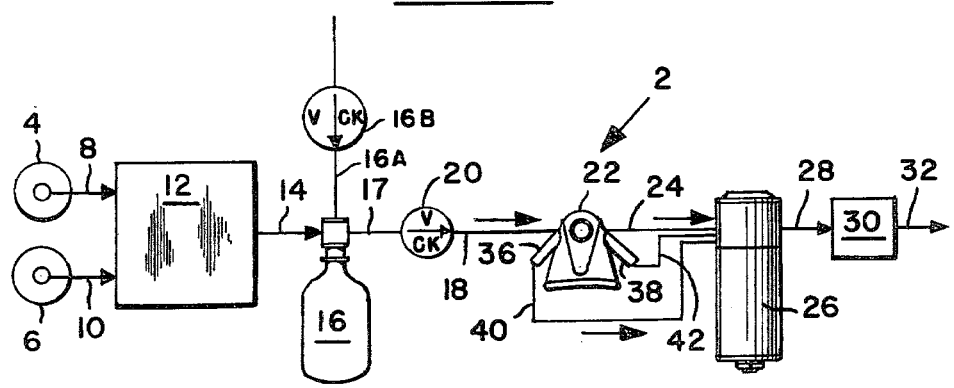
FIG. 6.

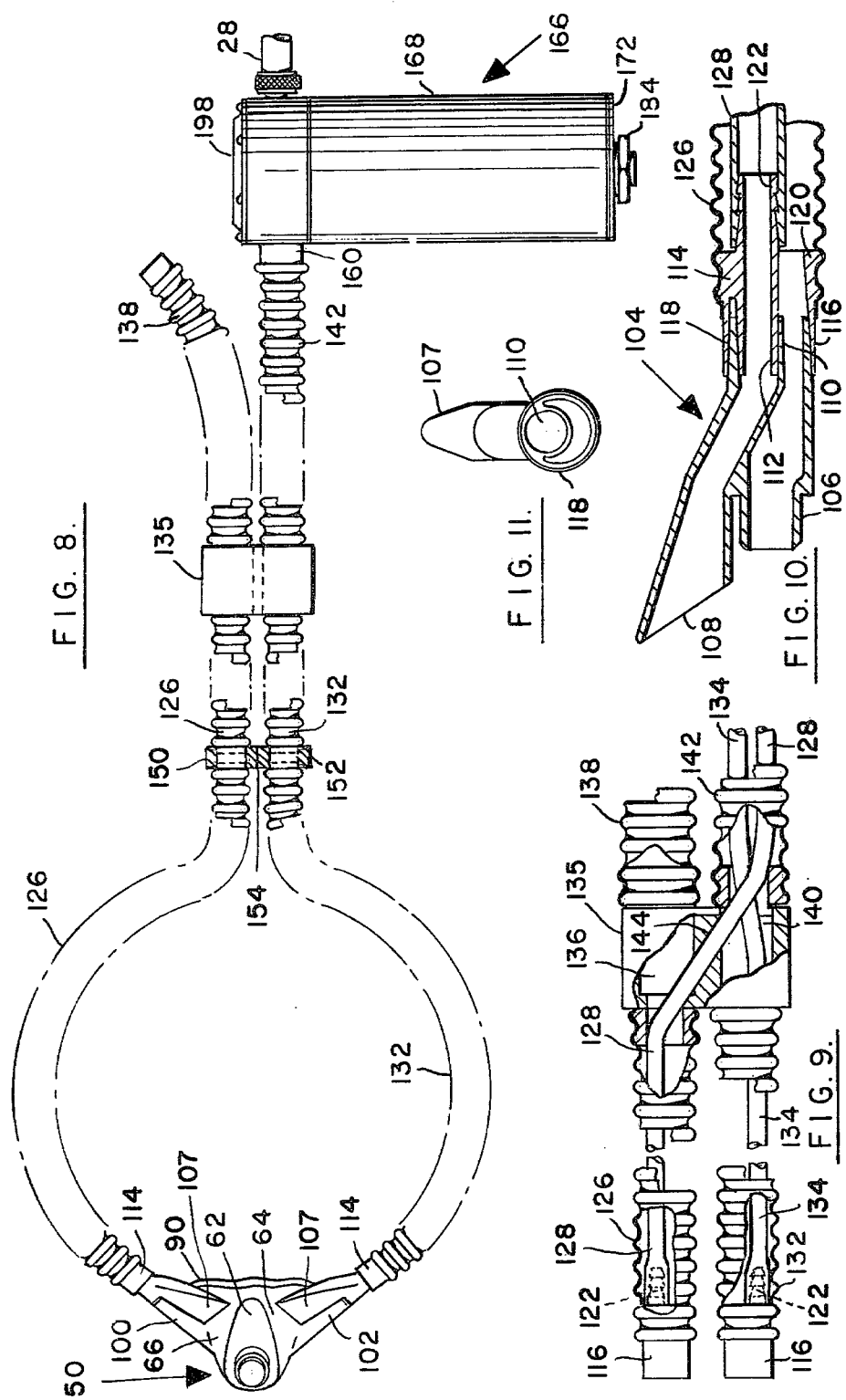

DEVICE FOR ADMINISTERING AN ANESTHETIC GAS

TECHNICAL FIELD

This invention is in the field of Devices for Administering Anesthesia.

BACKGROUND OF THE PRIOR ART

While there is no evidence of harm to patients from exposure to anesthetic gases such as nitrous oxide, some studies suggest that such gases may be detrimental to the health of dental personnel who are exposed to them. Thus, for example, dental personnel exposed to anesthetic gas have been found to have significantly more kidney and liver disease than those who are not so exposed. Further, the incidence of spontaneous miscarriages with female dental workers exposed to anesthetic gas has been found to be higher than in the case of those not so exposed.

Efforts have been made in the past to design systems for administering an anesthetic gas which prevent the escape of gas to the atmosphere where it can be inhaled by dental personnel. Thus, there is disclosed in U.S. Pat. No. 4,015,598, the disclosure of which is incorporated herein by reference, a nasal mask having a second outer wall to form an exhaust passage communicating with the inner portion of the mask and having an open lower peripheral edge for scavenging gas leaking from the mask, the said exhaust passage being connected to a source of vacuum. Such prior art masks in systems for administering anesthetic gas involve a number of problems. Patient breathing is not always well adjusted to the capacity of the vacuum system. If the patient breathes out more than the vacuum system can handle, the patient blows the mask away from his face and nose permitting anesthetic gas to be discharged into the atmosphere. On the other hand, if the vacuum capacity is too great, it draws from the breathing bag wasting anesthetic gas. Further, the prior art face masks do not fit closely on many patients resulting in the unwanted escape of anesthetic gas and tending to cause unwanted marking of the patient's skin since they tend to be strapped on very tightly to prevent the unwanted escape of anesthetic gas.

Another prior art technique is to cover the patient's head including the nasal mask with a hood having a negative pressure within the hood. However, the hood is inconvenient for dental personnel and is objectionable to the patient when awake.

The problems of blowing the mask off the face and unnecessarily withdrawing anesthetic gas from the breathing bag have been solved by this invention by providing a reservoir in the vacuum system. In addition, the invention provides scavenging nozzles for the face mask which are connected to the vacuum system by lines separate from the lines accommodating the patient's exhalation thus preventing exhalation to the atmosphere through the scavenging system as is possible with the prior art mask first described above. Further, the invention provides a mask which can be adjusted so as to fit the particular patient to which it is to be applied.

BRIEF SUMMARY OF THE INVENTION

A system for administering an anesthetic gas to a patient has a mask, means for supplying an anesthetic gas to the mask when the patient inhales, and an exhaust line having its proximal end connected to the mask and adapted to have its terminal end connected to a source of vacuum to exhaust gas from the mask when the patient exhales. A closed reservoir is in series with said exhaust line between the proximal and terminal ends thereof. The reservoir has an inlet and an outlet with a check valve adjacent to the inlet which is closed when the patient inhales. Advantageously, the reservoir check valve is a diaphragm valve and the face mask has at least one nozzle for scavenging gas escaping from the mask.

BRIEF DESCRIPTION OF THE DRAWINGS

FIG. 1 is a side perspective view of a face mask in accordance with the invention;

FIG. 2 is a rear elevation of the mask of FIG. 1;

FIG. 3 is a rear elevation of the mask of FIG. 1 showing it adjusted to a different position;

FIG. 4 is a section taken on the plane indicated by the line 4—4 in FIG. 2;

FIG. 5 is a side elevational view showing the mask over a patient's nose and being adjusted to the patient;

FIG. 6 is a schematic view of a system for administering an anesthetic gas in accordance with the invention;

FIG. 7 is a vertical section through a reservoir in accordance with the invention;

FIG. 7a is a horizontal section, partially broken away, through two connecting fittings of the reservoir of FIG. 7;

FIG. 8 is an elevational view of a portion of a device for administering an anesthetic gas in accordance with the invention;

FIG. 9 is a view, partially broken away, of a portion of the hoses of the system of FIG. 8;

FIG. 10 is a sectional view through a scavenging nozzle fitting of the face mask of FIG. 1, and FIG. 11 is an outer end view of the scavenging nozzle of FIG. 10.

DETAILED DESCRIPTION

Adverting first to FIG. 6, a system 2 in accordance with the invention for administering an anesthetic gas to a patient has a tank 4 of oxygen and a tank 6 of an anesthetic gas, for example, nitrous oxide, which are respectively connected by lines 8 and 10 to gas flow control apparatus 12 which controls the ratio of the two gases and the rate of flow of the mixture of the gases. Apparatus 12 is connected by line 14 to a breathing bag 16 which, in turn, is connected to an output line 17 connected to a check valve 20. Bag 16 is also connected to an air line 16A having a check valve 16B to provide air to the patient if there is an interruption in the normal gas supply. Line 18 is connected to check valve 20 and is connected to the interior of an anesthetic mask 22 which, in turn, is connected by line 24 to a closed reservoir 26 connected to a vacuum pump 30 by a line 28. Vacuum pump 30 discharges through line 32 to the atmosphere outside of the room in which the system is located, preferably outside of the building in which the room is located. Mask 22 has a pair of scavenging nozzles 36 and 38 for picking up any gas escaping from the mask. Scavenging nozzles 36 and 38 are connected respectively by lines 40 and 42 to reservoir 26.

A mask 50 in accordance with the invention is shown in FIGS. 1 through 5. It has a generally cup-shaped wall 60 of a resilient gas impermeable material, for example rubber or silicone rubber, and has a front portion 62 and side portions 64 and 66. In front portion 62, there is an opening 70 accommodating an air admission valve 72 of a conventional type having a rotating ring 74 with an opening 76 cooperating with inlet opening 77 for adjusting the amount of air admitted to the mask, and a rubber diaphram check valve 78 secured to a stem 79 to permit the entry of air into the mask and block the outflow of air. The employment of valve 72 is not necessary for the successful operation of mask 50. Integral with wall 60 is a bead 90 of resilient gas impermeable material, for example, rubber or silicone rubber, the bead 90 outlining an opening 92 for the reception of the patient's nose. A deformable metal strip 94, for example, a copper wire of about 2 millimeters in diameter, is molded in bead 90 in the portion thereof adapted to be opposite the patient's nose in order to permit bead 90 to be set in a position conforming to the patient's nose.

Molded integrally with wall 60 are a gas inlet tube 100 and a gas discharge tube 102. Attached to each of these tubes is a connection member 104 having a male portion 106 adapted to fit inside tube 100 or 102 as may be the case. Integral with each connector 104 is a scavenging nozzle 107 having an end 108 adapted to be positioned close to a side portion of wall 60 and an end 110 adapted to receive a tubular portion 112 of an adapter fitting 114 (FIG. 10) which has a female portion 116 which is telescoped over the corresponding male portion 118 of member 104. Fitting 114 has a corrugated portion 120 which receives and retains a corrugated hose. Tubular portion 112 has a male end 122 for the reception and retention of a tube. Fitting 114 associated with the member 104 connected to tube 100 is connected to a hose 126 (FIG. 9) of corrugated resilient material, for example, rubber. Male end 122 is connected to a flexible tube 128 (FIG. 10).

The fitting 114 associated with the member 104 connected to tube 102 similarly connected to a flexible corrugated hose 132 with its male end 122 connected to a flexible tube 134 (FIG. 9). Hoses 126 and 132 are respectively connected to a cross-over member 135 (FIG. 9) which has a passage 136 communicating with hose 126 and also with a flexible corrugated hose 138 secured to cross-over member 135. Likewise, cross-over member 135 has a passage 140 communicating with hose 132 and also with a flexible corrugated hose 142 connected to cross-over member 135. Tube 134 passes through cross-over member 135 through passage 140 into hose 142. Tube 128 passes into passage 136 and then through cross-over passage 144 with which it makes a tight fit into passage 140 and thence into tube 142.

Hoses 126 and 132 also pass through openings 150 and 152 in a conventional locking sleeve member 154. Member 154 is positioned to hold the hoses around the patient's head snuggly so as to act to hold the face mask 50 against the patient's face and nose.

Hose 138 is connected to a system for supplying an anesthetic gas, for example, being connected to the check valve 20 in the system shown in FIG. 6. Hose 142 has an end 160 which is connected to a connecting member 162 (FIG. 7) secured to a cap 164 of an enclosed reservoir 166. Cap 164 is mounted on a cylindrical member 168 with a gasket 170 therebetween. A bottom plate 172 is mounted on the other end of member 168 with a gasket 174 therebetween. A bolt member 178 has its upper end threadably connected at 180 to cap 164 in a bore 182 therein. The other end of bolt member 178 is threadably connected to a nut 184 which is threaded up against a ring gasket 186. Bolt member 178 has a plurality of openings 190 in its lower end to provide for passages between the interior of the reservoir and a bore 191 in bolt member 178 extending from the upper end of the bolt member to just below openings 190.

The interior of connecting member 162 communicates with a chamber 190 in cap 164. The upper boundary of chamber 190 is formed by a flexible diaphram 192 of, for example, rubber which overlies a reduced diameter portion 194 of bore 182 to form a valve. Diaphram 192 is secured by a cap member 198 secured to cap 164 by machine screws indicated at 200. Cap 198 has a vent to the atmosphere 202. It will be seen that the area of diaphram 192 exposed to chamber 190 is far greater than the area exposed to the interior of the reduced diameter portion 194 of bore 182 in order to permit a relatively low pressure of exhaled gases to raise diaphram 192 and overcome the negative pressure applied to the diaphram in reduced diameter portion 194 in order to insure free exhausting of exhaled gases, while preventing the vacuum system from withdrawing gases from the mask during inhalation by the patient. Advantageously, the ratio of the area of the diaphram 192 exposed to chamber 190 to the area exposed to the interior of reduced diameter portion 194 will be from about 40 to 1 to about 50 to 1.

Bore 182 is in communication with a passage 206 in cap 164 to which is secured a fitting 208 to which a line 210 is removably connected. Line 210 is adapted to be connected to a source of vacuum with a discharge outside of the room in which the patient is located and may, for example, be connected to the pump 30 shown in FIG. 6.

Lines 128 and 134 are connected to connecting fittings 220 and 222 which are secured to cap 164 and communicate with a passage 224 in cap 164 which in turn communicates with the interior of the reservoir.

OPERATION

In operation, the system supplying gas to hoses 138, 126 and mask 22, for example, the gas regulating system 12 and breathing bag 16, are activated and the source of vaccum for reservoir 26 such as the pump 30 of FIG. 6 is started. The mask 50 with the bead 90 opened out as shown in FIG. 2 is then placed over the nose of the patient and the bead is squeezed in gently so as to fit snuggly about the patient's nose without closing the nostrils. This causes the deformation of strip 94 which then retains the bead in its position conforming to the patient's nose. The mask is held in place by positioning member 154 to hold hoses 126 and 132 snuggly against the patient's head. The patient commences to breath in the desired mixture of, for example, oxygen and nitrous oxide through tube 100. The patient's exhalations pass into tube 102, hose 132 and thence through the cross-over member 134 into tube 142 and into chamber 190 where the increase in pressure causes diaphram 192 to lift permitting the exhaled gases to pass into bore 182. If the patient's exhalations are relatively light, the exhaled gases will be withdrawn immediately through passage 206, and line 210, and discharged to the atmosphere. If the exhalations are sufficiently heavy to exceed the capacity of pump 30 to withdraw them, the excess not withdrawn will pass down through the interior of bolt member 178 and, if sufficiently voluminous, through openings 190 into the interior of the reservoir. When the patient inhales, the pressure in chamber 190 will drop permitting diaphram 192 to close off reduced diameter portion 194 and pump 30 will continue to withdraw gas from the reservoir. Since nitrous oxide is heavier than air and will lie below the oxygen inside the reservoir, the nitrous oxide in the reservoir will be withdrawn first. It will be appreciated that since the volume of exhalation in excess of what can be handled by the pump 30 are received in the reservoir 166, the patient does not blow the nasal mask away from his nose and face, thus the minimum of gas escapes from between the mask and the patient. This escape is further reduced by the employment of the rounded bevel 90 and deformable metal strip 94 which provide a close fit of the mask 50 to the patient. Since the pair of scavenger nozzles 104,104 are also connected to reservoir 166, any gases around the side portions 64 and 66 of the mask are withdrawn into the scavenger nozzles and conveyed to reservoir 166 through tubes 128 and 134, and thence are discharged to the atmosphere by the action of pump 30.

It will be understood that the above described embodiments are illustrative and are not intended to be limiting.

I claim:

1. In a system for administering an anesthetic gas to a patient having a mask, means for supplying an anesthetic gas to said mask when the patient inhales, an exhaust line having its proximal end connected to the mask and adapted to have its terminal end connected to a vacuum system for exhausting gas from the mask to a remote atmosphere when the patient exhales, the improvement comprising:

a closed reservoir having an inlet opening and an outlet opening connected in series with said exhaust line between the proximal and terminal ends thereof comprising a hollow body having an open end, a cap closing the open end and including said inlet opening connected to the portion of the exhaust line upstream of the reservoir, said outlet opening communicating said reservoir with a portion of the exhaust line downstream of the reservoir, an outlet valve mounted within said cap and having an inlet communicating with said inlet opening and an outlet communicating with said reservoir, said inlet defining a valve seat, a diaphragm mounted adjacent said seat in the cap with its periphery secured to the cap, said diaphragm being located in said cap such that one side of the diaphram is adapted to contact said seat and said inlet opening communicates with an area of said one side of the diaphram which is substantially larger than the area of the diaphram adapted to contact the valve seat to keep the diaphram against the valve seat when the patient is inhaling and to allow a free flow of gas when the patient is exhaling.

2. In a system for administering an anesthetic gas to a patient having a mask, means for supplying an anesthetic gas to said mask when the patient inhales, an exhaust line having its proximal end connected to the mask and adapted to have its terminal end connected to a vacuum system for exhausting gas from the mask to a remote atmosphere when the patient exhales, the improvement comprising:

a closed reservoir having an inlet opening and an outlet opening connected in series with said exhaust line between the proximal and terminal ends thereof comprising a hollow body having an open end, a cap closing the open end and including said inlet opening connected to the portion of the exhaust line upstream of the reservoir, said outlet opening communicating said reservoir with the portion of the exhaust line downstream of the reservoir, an outlet valve mounted within said cap and having an inlet communicating with said inlet opening and an outlet communicating with said reservoir, said inlet defining a valve seat, a diaphragm mounted adjacent said seat in the cap with its periphery secured to the cap, said diaphragm being located in said cap such that one side of the diaphram is adapted to contact said seat and said inlet opening communicates with an area of said one side of the diaphram which is substantially larger than the area of the diaphram adapted to contact the valve seat to keep the diaphram against the valve seat when the patient is inhaling and to allow a free flow of gas when the patient is exhaling, a depending tube extending from said outlet of said outlet valve to the bottom of the reservoir and having an opening at the bottom of the tube providing communication with the interior of the reservoir, the upper end of the tube being connected to the outlet opening of the reservoir.

3. In a system for administering an anesthetic gas to a patient having a mask, means for supplying an anesthetic gas to said mask when the patient inhales, an exhaust line having its proximal end connected to the mask and adapted to have its terminal end connected to a vacuum system for exhausting gas from the mask to a remote atmosphere when the patient exhales, the improvement comprising:

a closed reservoir in series with said exhaust line between the proximal and terminal ends thereof, said reservoir having an inlet connected to the portion of the exhaust line upstream of the reservoir and an outlet connected to the portion of the exhaust line downstream of the reservoir, means in said reservoir for preventing the flow of gas through the inlet when the patient inhales, and a nozzle secured to one side of the face mask for scavenging gas escaping from the mask and a second exhaust line connecting said nozzle directly to the reservoir downstream of the flow preventing means.

4. The system of claim 3 having a second nozzle secured to the other side of the face mask for scavenging gas escaping from the mask and a third exhaust line connecting said second nozzle directly to the reservoir downstream of the flow preventing means.

5. A device for administering an anesthetic gas to a patient comprising:

a mask, a first line connected to the mask and adapted to be connected to an anesthetic gas supply system, a gas reservoir having an outlet adapted to be connected to a vacuum exhaust system and an inlet, an exhaust line having one end connected to the mask and the other end connected to the reservoir inlet, means in said reservoir for preventing the flow of gas through the inlet when the patient inhales, and a nozzle secured to one side of the face mask for scavenging gas escaping from the mask and a second exhaust line connecting said nozzle directly to the reservoir downstream of the flow preventing means.

6. The system of claim 5 having a second nozzle secured to the other side of the face mask for scavenging gas escaping from the mask and a third exhaust line connecting said second nozzle directly to the reservoir downstream of the flow.

7. A device for administering an anesthetic gas to a patient comprising:
   a mask,
   a first line connected to the mask and adapted to be connected to an anesthetic gas supply system,
   a gas reservoir having separated upper and lower portions and having an outlet adjacent the upper end of the lower portion adapted to be connected to a vacuum exhaust system and an inlet in the upper portion,
   an exhaust line having one end connected to the mask and the other end connected to the reservoir inlet,
   means for preventing the flow of gas through the exhaust line when the patient inhales,
   a nozzle secured to one side of the face mask for scavenging gas escaping from the mask and a second exhaust line connecting said nozzle directly to the upper end of the lower portion of the reservoir, and
   a tube connecting the upper and lower portions of the reservoir and having an opening adjacent the bottom of the lower portion of the reservoir.

* * * * *